United States Patent [19]

Bulidon et al.

[11] 4,277,607
[45] Jul. 7, 1981

[54] PROCESS FOR THE PREPARATION OF 4-CHLOROQUINOLINES

[75] Inventors: Jacques Bulidon, Paris; Charles Pavan, Nogent-sur-Marne, both of France

[73] Assignee: Roussel Uclaf, Paris, France

[21] Appl. No.: 942,652

[22] Filed: Sep. 15, 1978

[30] Foreign Application Priority Data

Oct. 7, 1977 [FR] France .................. 77 30249

[51] Int. Cl.³ .................. C07D 215/18; C07D 215/12; C07D 215/20; C07D 215/36
[52] U.S. Cl. ...................................... 546/179; 546/180; 562/452
[58] Field of Search ......... 260/283 SY, 283 R, 283 S; 546/179, 180

[56] References Cited

U.S. PATENT DOCUMENTS

| | | | |
|---|---|---|---|
| 2,451,610 | 10/1948 | Campbell | 260/283 SY |
| 2,478,125 | 8/1949 | Morthey et al. | 260/283 SY |
| 2,785,165 | 3/1957 | Schock et al. | 260/283 SY |
| 3,567,732 | 3/1971 | Soly et al. | 546/180 |

FOREIGN PATENT DOCUMENTS 1514280  1/1967  France .

OTHER PUBLICATIONS

Rügheimer, "Berichte", vol. 17, pp. 736–739 (1884) cited in Hollins "Syn. of Org. Nitrogen Cmpds.", p. 271 (1924).
Mathieu et al., "Cahiers de Synthese Organique", vol. VII, pp. 151–160 (1961).
Rügheimer, Ber., (1886) 19 p. 1172, cited in C. Hollins, "Synthesis of Nitrogen Ring Compounds", p. 331 (1924).

Primary Examiner—Donald G. Daus
Assistant Examiner—D. B. Springer
Attorney, Agent, or Firm—Hammond & Littell, Weissenberger and Muserlian

[57] ABSTRACT

Novel process for the preparation of 4-chloroquinolines of the formula

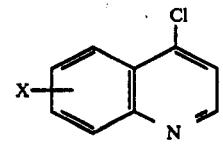

wherein X is in the 5,6,7 or 8-position and is selected from the group consisting of hydrogen, methyl, halogen, $CF_3-$, $CF_3O-$ and $CF_3S-$ by reacting a compound of the formula

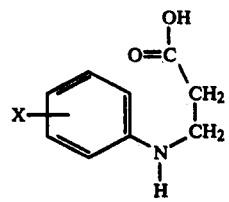

or a functional derivative thereof with a chlorination agent in the presence of an oxidation agent and to a novel intermediate.

7 Claims, No Drawings

PROCESS FOR THE PREPARATION OF 4-CHLOROQUINOLINES

STATE OF THE ART

The products of formula I are known and are used as starting materials to synthesize compounds having pharmacological properties, such as in the synthesis of 4-(2'-alkoxycarbonyl-phenylamino)-quinolines as described by Allais et al [Chimie Therapeutique, Vol. 8(2) (1973), p. 154–68]. The products of formula I have been prepared, for example, by the process described in French Pat. No. 1,584,746 wherein suitably substituted aniline derivatives are condensed with ethyl ethoxyallylacetate, ethyl ethoxymethylene malonate, β-propiolactone or acrylic acid, cyclizing the condensed product, saponifying the resulting product to form a free carboxyl group, decarboxylating the resulting product, replacing the 4-hydroxyl group with a chlorine atom with a chlorination agent with eventual deshydration.

Another example for the preparation of 4-chloro-8-trifluoromethyl-quinoline in 5 steps comprises condensing o-trifluoromethyl-aniline with ethyl ethoxymethylene malonate to form ethyl o-trifluoromethylanilinomethylene-malonate, cyclizing the latter to form 3-carbethoxy-4-hydroxy-8-trifluoromethyl-quinoline, saponifying the latter to form 3-carboxy-4-hydroxy-8-trifluoromethyl-quinoline and reacting the latter with phosphorus oxychloride to form the desired product.

The compounds of formula I wherein X is chlorine may be prepared by another way such as the process described in French Pat. No. 1,514,280 by cyclizing a 3-(chloroanilino)-propanoic acid of the formula

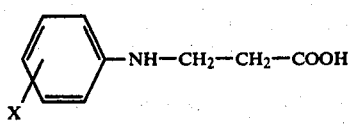

with a polyphosphoric acid to obtain a 4-oxo-chloro-1,2,3,4-tetrahydroquinoline of the formula

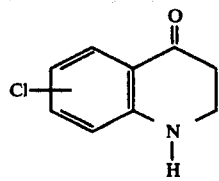

which is then reacted with a chlorination agent in the presence of a oxidizing agent to obtain the corresponding 4-dichloroquinoline.

OBJECTS OF THE INVENTION

It is an object of the invention to provide a novel process for the direct production of the compounds of formula I starting from the acids of formula II.

It is another object of the invention to provide a novel intermediate product.

These and other objects and advantages of the invention will become obvious from the following detailed description.

THE INVENTION

The novel process of the invention for the preparation of 4-chloro-quinolines of the formula

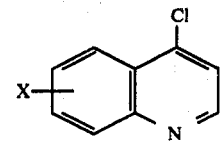

wherein X is in the 5,6,7 or 8-position and is selected from the group consisting of hydrogen, methyl, halogen, $CF_3-$, $CF_3O-$ and $CF_3S-$ comprises reacting an acid of the formula

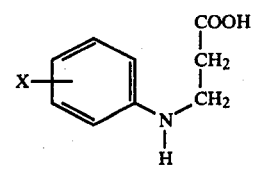

or a functional derivative thereof with a chlorination agent in the presence of an oxidation agent to form the desired compound of formula I.

The process of the invention is a sure and simple technique which gives excellent yields while avoiding the formation of 4-oxo-1,2,3,4-tetrahydroquinolines such as 4-oxo-8-trifluoromethyl-1,2,3,4-tetrahydroquinoline which are unstable in hot phosphoric acid media. For example, it is possible to prepare 4-chloro-8-trifluoromethyl-quinoline directly from β-(o-trifluoromethylanilino)-propanoic acid in yields on the order of 80% which is a yield on the order of 63% in 2 steps beginning from o-trifluoromethyl-analine while if 4-chloro-8-trifluoromethyl-quinoline is prepared by the process of French Pat. No. 1,584,746, 5 steps are required and the yields are clearly inferior.

Examples of suitable chlorination agents are phosphorus oxychloride, phosphorus pentachloride and thionyl chloride. The oxidation agent may be the oxygen in air, iodine or a halogen derivative such as cupric chloride or ferric chloride. The preferred functional derivatives of the acids of formula II are the acid anhydride, acid chloride or an alkyl ester thereof.

In a preferred mode of the process of the invention, the compound of formula II has the structure

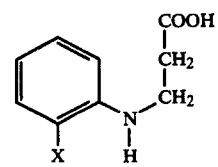

and most preferably, X is $CF_3$. The acid form is preferably used and the chlorination agent is phosphorus oxychloride in the presence of iodine.

The acids of formula II are generally known and can be prepared by known processes such as those described in French Pat. No. 1,514,280.

In the following examples there are described several preferred embodiments to illustrate the invention. However, it should be understood that the invention is not intended to be limited to the preferred embodiments.

EXAMPLE

4-chloro-8-trifluoromethyl-quinoline

STEP A: β-(o-trifluoromethylaniline)-propanoic acid 672 g of acrylic acid were added to 500 g of o-trifluoromethylaniline at 20°–25° C. with stirring while bubbling nitrogen therethrough and then 0.5 g of hydroquinone were added thereto in the dark. The mixture was heated to 75° C. over one hour and was then held at 75° C. for 32 hours. The mixture was cooled to 65°–70° C. and 500 ml of technical cyclohexane and 500 ml of demineralized water were rapidly added thereto. The mixture was refluxed for 10 minutes and was then slowly cooled to 2° to 4° C. and held there for one hour. The mixture was vacuum filtered and the recovered crystals were washed and dried to obtain 636.7 g of β-(o-trifluoromethylanilino)-propanoic acid.

STEP B: 4-chloro-8-trifluormethyl-quinoline 13.75 g of monosublimated iodine were added at 0° to 5° C. to 75 ml of phosphorus oxychloride and the mixture was heated over 30 minutes to 93°–95° C. and was held at 93°–95° C. for about 30 minutes. Then, 50 g of the product of Step A were added over 6 minutes in fractions of 1.250 g to the mixture and then the mixture was held at 93°–95° C. for 30 minutes. After cooling to 70°±5° C., the mixture was added over about 30 minutes to a stirred solution of 11 g of sodium bisulfite in 875 ml of water held at 40° to 45° C. The mixture was cooled over 30 minutes to 15°–20° C. to obtain a gummy suspension which was vacuum filtered washed and dried. The product was crystallized from methanol to obtain 36.9 g of 4-chloro-8-trifluoromethyl-quinoline with a 98% purity.

Various modifications of the products and processes of the invention may be made without departing from the spirit or scope thereof and it is to be understood that the invention is intended to be limited only as defined in the appended claims.

We claim:

1. A process for the preparation of 4-chloro-quinolines of the formula

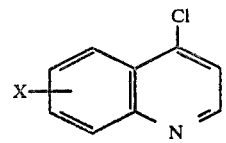

wherein X is in the 5,6,7 or 8-position and is selected from the group consisting of hydrogen, methyl, halogen, $CF_3-$, $CF_3O-$ and $CF_3S-$ consisting essentially of reacting an acid of the formula

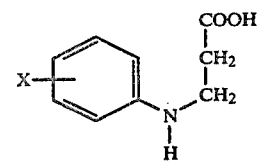

with a chlorination agent selected from the group consisting of phosphorus oxychloride, phosphorus pentachloride and thionyl chloride in the presence of an oxidation agent selected from the group consisting of oxygen, iodine, cupric chloride and ferric chloride to form the desired compound.

2. The process of claim 1 wherein the starting material has the formula

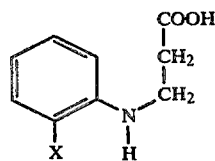

3. The process of claim 1 wherein X is $CF_3-$.

4. The process of claim 1 wherein the chlorination agent is phosphorus oxychloride.

5. The process of claim 1 wherein the oxidation agent is iodine.

6. The process of claim 1 wherein the chlorination agent is phosphorus oxychloride and the oxidation agent is iodine.

7. The process of claim 1 wherein β-(o-trifluoromethylanilino)-propanoic acid is reacted with phosphorus oxychloride in the presence of iodine.

* * * * *